US00PP17029P2

(12) United States Plant Patent
Danziger

(10) Patent No.: US PP17,029 P2
(45) Date of Patent: Aug. 22, 2006

(54) *CALIBRACHOA* PLANT NAMED 'DANCALDARPINK'

(50) Latin Name: ***Calibrachoa* sp.**
Varietal Denomination: Dancaldarpink

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 25 days.

(21) Appl. No.: 11/144,614

(22) Filed: Jun. 6, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Foley & Lardner LLP

(57) ABSTRACT

A new and distinct cultivar of *Calibrachoa* plant named 'Dancaldarpink' characterized by having medium, purple-red colored flowers; a vigorous, cascading growth habit; a very floriferous flowering habit with a long blooming season; and is suitable for patio and outdoor plant beddings.

2 Drawing Sheets

Botanical designation: *Calibrachoa* sp.
Variety denomination: 'Dancaldarpink'.

BACKGROUND OF THE INVENTION

The present invention relates to a new and distinct cultivar of *Calibrachoa* plant, botanically known as *Calibrachoa* sp., hereinafter referred to by the cultivar name 'Dancaldarpink'.

The new *Calibrachoa* cultivar is a product of a planned breeding program conducted by the Inventor, Gabriel Danziger, in Moshav Mishmar Hashiva, Israel. The objective of the breeding program was to develop a new *Calibrachoa* cultivar having attractive flower colors, a desirable plant habit, and a strong, vigorous growth habit.

The new *Calibrachoa* cultivar originated from a cross made in a controlled breeding program by the Inventor in 2003 in Moshav Mishmar Hashiva, Israel. The female or seed parent is a *Calibrachoa* sp. designated as 'CV.217' (unpatented). The male or pollen parent is a *Calibrachoa* sp. designated as 'CV.100' (unpatented). 'Dancaldarpink' was discovered and selected by the Inventor in February of 2003 as a flowering plant within the progeny of the stated cross in a controlled environment in Moshav Mishmar Hashiva, Israel.

Asexual reproduction of the new cultivar by stem tip cutting was first performed in May of 2003 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'Dancaldarpink' which in combination distinguish this *Calibrachoa* as a new and distinct cultivar:

1. Medium, purple-red colored flowers;
2. Vigorous, cascading growth habit;
3. Very floriferous flowering habit with a long blooming season; and
4. Suitable for patio and outdoor plant beddings.

Plants of the new *Calibrachoa* cultivar 'Dancaldarpink' differ from plants of the parents, 'CV.217' (unpatented) and 'CV.100' (unpatented) in the following characteristics described in Table 1.

TABLE 1

| Trait | New Cultivar 'Dancaldarpink' | Female Parent 'CV.217' (unpatented) | Male Parent 'CV.100' (unpatentcd) |
|---|---|---|---|
| Corolla color | Purple-red | Pink | Purple |
| Corolla size | Medium<br>Diameter:<br>2 to 2.5 cm | Small<br>Diameter:<br>1.5–2 cm | Medium<br>Diameter:<br>2 to 2.5 cm |

Of the many commercial cultivars known to the present Inventor, the most similar in comparison to the new *Calibrachoa* cultivar 'Dancaldarpink' is the *Calibrachoa* cultivar 'Calimor White' (unpatented). In side-by-side comparisons conducted in Moshav Mishmar Hashiva, Israel, plants of 'Dancaldarpink' differed from plants of 'Calimor White' primarily in corolla color. Plants of 'Dancaldarpink' also differed from plants of 'Calimor White' in the traits described in Table 2.

TABLE 2

| Trait | New Cultivar 'Dancaldarpink' | Comparison Cultivar 'Calimor White' |
|---|---|---|
| Corolla color: | Purple-Red | White |
| Corolla size: | Medium<br>Diameter: 2 to 2.5 cm | Medium<br>Diameter: 2 to 2.5 cm |

BRIEF DESCRIPTION OF THE DRAWINGS

The accompanying photographic drawings illustrate the overall appearance of the new *Calibrachoa* cultivar 'Dancaldarpink' showing the colors as true as is reasonably possible with colored reproductions of this type. Colors in the photographs may differ slightly from the color values cited in the detailed botanical description which accurately describe the color of the 'Dancaldarpink'.

The first photograph shows a side perspective view of a typical flowering plant of 'Dancaldarpink' in a hanging planter at 3 months of age.

The second photograph shows a close-up view of the typical flowers and leaves of 'Dancaldarpink' at 3 months of age.

DETAILED BOTANICAL DESCRIPTION

The new *Calibrachoa* cultivar 'Dancaldarpink' has not been observed under all possible environmental conditions. The phenotype of the new cultivar may vary with variations in environment such as temperature, light intensity, and daylength without any change in the genotype of the plant.

The aforementioned photographs, together with the following observations, measurements and values describe plants of the new cultivar 'Dancaldarpink' as grown in a greenhouse in Moshav Mishmar Hashiva, Israel, under conditions which closely approximate those generally used in commercial practice. Plants of 'Dancaldarpink' are grown outdoors in moderate climate and grown indoors during winter. Irrigation and fertilization are needed on a regular basis. For optimal growth, grow plants of 'Dancaldarpink' in full sunlight. Plants of 'Dancaldarpink' are fully grown plant in 3 months when grown in full sunlight, and bloom all year-round in a moderate climate. 'Dancaldarpink' is used as a pot plant and a bedding plant.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 3 months.

Classification:
- *Botanical.*—*Calibrachoa* sp.
- *Commercial.*—*Calibrachoa* cv. Calimor Dark Pink.

Parentage:
- *Male parent.*—*Calibrachoa* cultivar designated 'CV.100' (unpatented).
- *Female parent.*—*Calibrachoa* cultivar designated 'CV.217' (unpatented).

Propagation:
- *Type.*—Cutting of side shoots.
- *Time and temperature to initiate and develop roots.*—Summer: 14 days at 18 to 27° C. Winter: 20 days at 18 to 22° C.
- *Rooting habit.*—From cutting base.

Plant:
- *General appearance and form.*—Vigorous, cascading growth habit with medium-sized, purple-red colored flowers.
- *Height.*—15 cm.
- *Spread.*—50 cm.
- *Growth and branching habit.*—Vigorous and high branching rate; cascading bush.

Lateral branches:
- *Quantity per plant.*—Hundreds.
- *Length.*—40 to 50 cm.
- *Diameter.*—About 0.1 cm.
- *Texture.*—Slight roughness.
- *Color.*—Green Group, RHS 140-B.
- *Internode length.*—About 2 cm.
- *Internode color.*—Green Group, RHS 140-B.
- *Average number of flowers per lateral branch.*—About 4.

Foliage:
- *Arrangement.*—Whorled.
- *Overall shape of leaf.*—Elliptic.
- *Apex.*—Obtuse.
- *Base.*—Acute.
- *Length.*—About 3 cm.
- *Width.*—About 1 cm.
- *Margin.*—Entire.
- *Texture.*—Puberulous.
- *Color of upper surface.*—Mature leaf: Green Group, RHS 137A. Immature leaf: Green Group, RHS 137A.
- *Color of lower surface.*—Mature leaf: Green Group, RHS 137C. Immature leaf: Green Group, RHS 137C.
- *Venation.*—Pattern: Pinnate (only the midrib can be seen). Color: Upper surface: Green Group, RHS 137C. Lower surface: Green Group, RHS 141C.
- *Petiole.*—None.

Flowers:
- *Flower type and habit.*—Single, horizontal facing, salverform flowers. Flowers persistent and not fragrant.
- *Flowering season.*—All year round in moderate climate.
- *Flowering response.*—Fully grown plant in 3 months.
- *Winter hardiness.*—Frost tender. Temperatures below 5° C. may damage plants.
- *Lastingness of the individual bloom.*—2 to 4 days.
- *Fragrance.*—None.
- *Bud.*—Rate of opening: About 2 to 4 days, according to weather. Length: The young bud is about 0.5 cm, and it lengthens to about 1.5 cm before opening. Diameter: About 0.4 cm. Shape: Tubular. Color: Immature Bud: Yellow Green Group, RHS 145-A. Mature bud: Purple Group, RHS 77-A.
- *Corolla.*—Arrangement and appearance: Single whorl of five petals, fused into flared trumpet. Corolla size: Diameter: 2.0 to 2.5 cm. Tube length: About 1.2 cm.
- *Petals.*—Petal Number: 5. Petal size: Length: About 2 cm. Width: 0.2 to 1.0 cm. Petal shape: Overall: Roughly spatulate to obovate. Apex shape: Obtuse. Base shape: Fused. Margin: Entire. Texture: Smooth. Petal color: When opening: Upper surface: Red-Purple Group, RHS N74B. Lower surface: Red-Purple Group, RHS N74D. When fully opened: Upper surface: Red-Purple Group, RHS N74B. Lower surface: Red-Purple Group, RHS N74D. Flower throat color (inside): Yellow Group, RHS 11B. Flower tube color (outside): Green-Yellow Group, Group 1-C.
- *Sepals.*—Arrangement and appearance: Single whorl of five sepals, fused at base. Sepal Number: 5. Sepal size: Length: About 1.5 cm. Width: About 0.4 cm. Sepal Shape: Overall: Oblong. Apex shape: Blunt. Base shape: Fused. Margin: Entire. Texture: Smooth. Sepal color: Upper surface: Green Group, RHS 137-A. Lower surface: Green Group, RHS 137-B.
- *Peduncles.*—Length: About 2.5 cm. Width: About 0.1 cm. Angle: About 45° from stem axis. Strength: Flexible. Texture: Smooth. Color: Green Group, RHS 143-B.

Reproductive organs:
- *Androecium.*—Stamen: Number: 5. Anther: Length: About 1.2 cm. Color: Yellow Group, RHS 12A. Pollen amount: Abundant. Pollen color: Yellow Group, RHS 12A.

*Gynoecium.*—Pistil: Number: 1. Length: About 1 cm. Stigma: Shape: Round. Color: Yellow-green Group, RHS 145 C. Style: Length: About 0.9 cm. Color: Green Group, RHS 143-C. Ovary: Color: Green Group, RHS 137C.

*Seeds.*—Length: About 0.1 cm. Width: About 0.05 cm. Shape: Ovoid. Texture: Smooth. Color: Brown (greyed-orange group), ranges from RHS 166A–C.

*Fruit.*—Length: About 0.5 cm. Width: About 0.3 cm. Shape: Globular. Texture: Smooth. Color: Green Group, RHS 137A.

Disease/pest resistance: No sensitivity was observed under regular growing conditions.

Disease/pest susceptibility: No information is currently available.

Low temperature tolerance: Sensitive to temperatures below 5° C.

I claim:

1. A new and distinct cultivar of *Calibrachoa* plant named 'Dancaldarpink', substantially as illustrated and described herein.

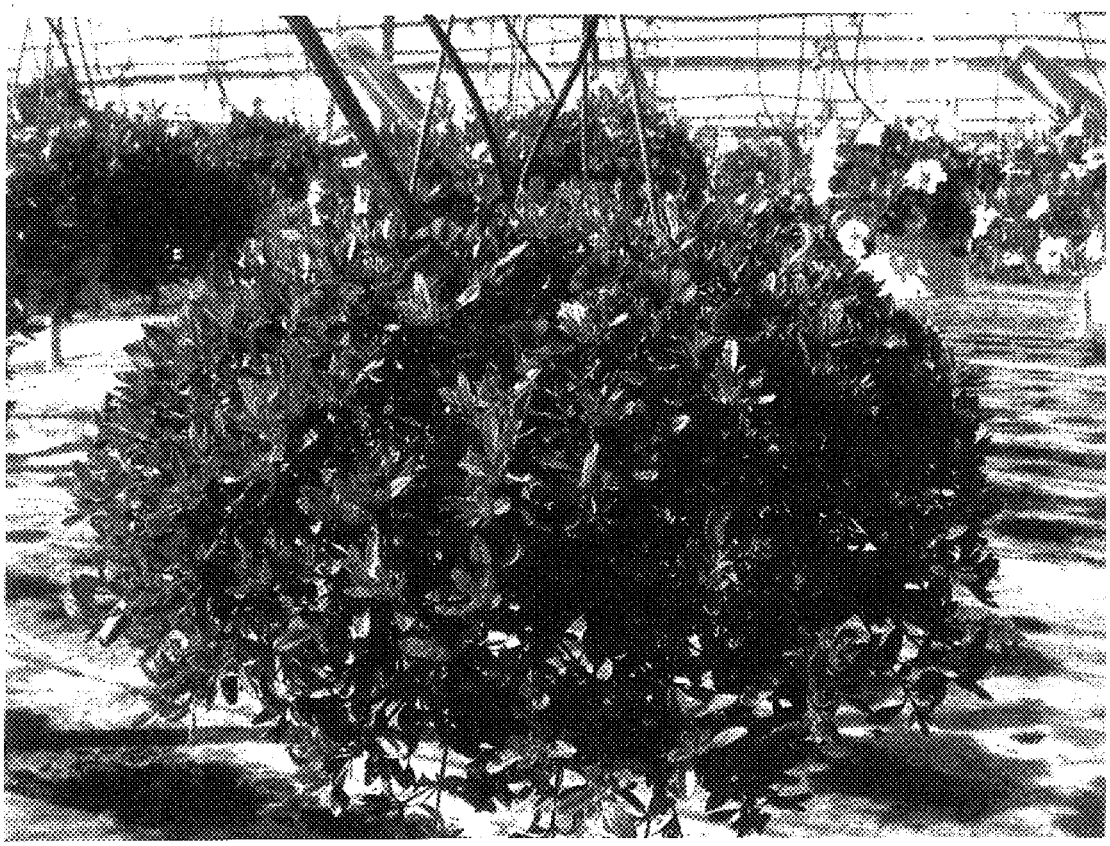

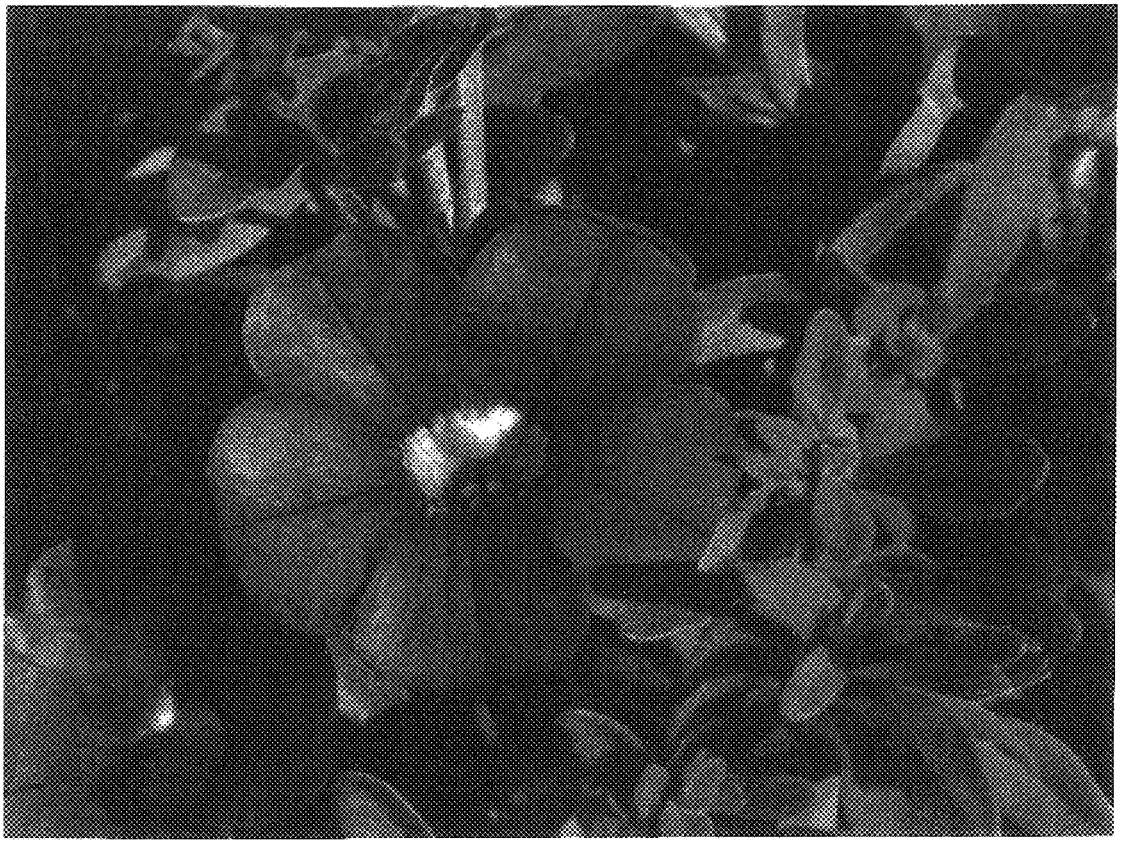

* * * * *